(12) United States Patent
Lai et al.

(10) Patent No.: US 9,588,103 B2
(45) Date of Patent: Mar. 7, 2017

(54) BIOLOGICAL PARTICLE ANALYZER AND METHOD OF ANALYZING BIOLOGICAL PARTICLES

(71) Applicant: Wistron Corporation, New Taipei (TW)

(72) Inventors: Chun-Chih Lai, New Taipei (TW); Ting-Wen Liu, New Taipei (TW)

(73) Assignee: Wistron Corporation, New Taipei (TW)

( * ) Notice: Subject to any disclaimer, the term of this patent is extended or adjusted under 35 U.S.C. 154(b) by 0 days.

(21) Appl. No.: 15/182,564

(22) Filed: Jun. 14, 2016

(65) Prior Publication Data

US 2016/0290993 A1 Oct. 6, 2016

Related U.S. Application Data

(62) Division of application No. 13/798,228, filed on Mar. 13, 2013, now Pat. No. 9,410,178.

(30) Foreign Application Priority Data

Jun. 22, 2012 (TW) .............................. 101122416 A

(51) Int. Cl.
*C12Q 1/00* (2006.01)
*G01N 15/00* (2006.01)
(Continued)

(52) U.S. Cl.
CPC ........... *G01N 33/4915* (2013.01); *C12Q 1/02* (2013.01); *G01N 15/12* (2013.01); *G01N 15/14* (2013.01);
(Continued)

(58) Field of Classification Search
CPC ........ C12Q 2565/629; C12Q 2563/149; C12Q 2563/155; B01L 2400/0415; B01L 2200/027; B01L 3/502761; B01L 2200/0668; G01N 15/1459; G01N 15/1429; G01N 15/12; G01N 15/1404
See application file for complete search history.

(56) References Cited

U.S. PATENT DOCUMENTS 5,495,105 A * 2/1996 Nishimura ............... H05H 3/04
250/222.2
7,057,712 B2 * 6/2006 Beck .................. G01N 15/1459
250/288

(Continued)

*Primary Examiner* — Lyle Alexander
*Assistant Examiner* — Bryan Kilpatrick
(74) *Attorney, Agent, or Firm* — Winston Hsu; Scott Margo

(57) ABSTRACT

A method of analyzing biological particles for a biological particle analyzer includes outputting a first detection result when at least one particle has arrived at the first detection area, outputting a second detection result to the control module when the particles have arrived at the second detection area, and determining when to turn on or off the light emission source and outputting a control signal to turn on or off the light emission source according to the first detection result, wherein a control module is configured to calculate a turn-on time according to different particle characteristics and an average velocity of the at least one particle, and the light emission source is turned on only when the at least one particle is being tested during the turn-on time.

12 Claims, 8 Drawing Sheets

(51) Int. Cl.
*G01N 15/14* (2006.01)
*G01N 33/49* (2006.01)
*G01N 15/12* (2006.01)
*C12Q 1/02* (2006.01)
*H01J 49/00* (2006.01)
*G01N 15/10* (2006.01)

(52) U.S. Cl.
CPC ..... G01N 15/1427 (2013.01); G01N 15/1434 (2013.01); *B01L 2200/027* (2013.01); *G01N 2015/105* (2013.01); *G01N 2015/1037* (2013.01); *H01J 49/0027* (2013.01)

(56) References Cited

U.S. PATENT DOCUMENTS

| | | | |
|---|---|---|---|
| 9,410,178 B2 * | 8/2016 | Lai | C12Q 1/02 |
| 2008/0003142 A1 * | 1/2008 | Link | B01F 3/0807 |
| | | | 422/82.08 |
| 2011/0089328 A1 * | 4/2011 | Li | B01L 3/50273 |
| | | | 250/364 |

* cited by examiner

BIOLOGICAL PARTICLE ANALYZER AND METHOD OF ANALYZING BIOLOGICAL PARTICLES

CROSS REFERENCE TO RELATED APPLICATIONS

This is a divisional application of U.S. application Ser. No. 13/798,228 filed on Mar. 13, 2013, which is included in its entirety herein by reference.

BACKGROUND OF THE INVENTION

1. Field of the Invention

The present invention relates to a biological particle analyzer and method of analyzing biological particles, and more particularly, to a biological particle analyzer and method of analyzing biological particles having a function of smart power savings.

2. Description of the Prior Art

A biological particle analyzer is widely used in basic research and clinical practice for Biology related fields including Cell biology, Oncology, Hematology, Immunology, Parmacology, Genetics and Diagnostics of Clinic Analysis. A Flow Cytometer is biophysical technology employed to perform simultaneously multiparametric analysis according to cell properties such as surface receptors and DNA by detecting scattered light from tested cells.

The Flow Cytometry utilizes a beam of laser light generated by a light emission source to directly light up the test cells, e.g. microparticles having a diameter 0.5-50 micrometers. Those cells attached to fluorescent chemicals are excited by the laser light to emit scatter lights, and the scatter lights are picked up by the electronic apparatus for quality and quantity analysis of the cells. Moreover, an advanced Flow Cytometer may perform sorting and selection to purify populations of interest cells to be reused for further application. Thus, the Flow Cytometer is widely used in experiments of Immunology, Microbiology and Cell biology.

In-Home Care or Telemedicine is becoming more and more popular nowadays as it helps people make simple health examinations, e.g. blood glucose measurements, in home or in distant rural communities. Thus, there is a need to design a portable Flow Cytometer.

However, when the traditional biological particle analyzer is operating, the light emission source of the biological particle analyzer or the Flow Cytometer consumes most of the power, and the light emission source is often turned on no matter whether a test procedure is being performed, which not only wastes power but also produces a significant amount of heat. For a portable Flow Cytometer, a battery having a high capacity is required, which increases a size/volume or production cost of the portable Flow Cytometer. Worse yet, the amount of heat may shorten battery life and influence usage convenience/reliability of the portable Flow Cytometer. Therefore, how to effectively reduce the power consumption of the light emission source and keep good performance of the portable Flow Cytometer has become a goal in the field.

SUMMARY OF THE INVENTION

It is therefore an object of the present invention to provide a biological particle analyzer and method of analyzing biological particles having a function of smart power savings.

The present invention further discloses a method of analyzing biological particles for a biological particle analyzer comprising a light emission source and a microchannel for containing a particle flowing inside the microchannel, the microchannel comprising a first detection area at an upstream location, a second detection area located at a downstream location and an excitation area at the downstream location lighted by the light emission source, the method comprising by a first detection circuit of the biological particle analyzer, outputting a first detection result when at least one particle has arrived at the first detection area; by a second detection circuit of the biological particle analyzer, outputting a second detection result to the control module when the particles have arrived at the second detection area; and by a control module of the biological particle analyzer, determining when to turn on or off the light emission source and outputting a control signal to turn on or off the light emission source according to the first detection result; wherein the control module is configured to calculate a turn-on time according to different particle characteristics and an average velocity of the at least one particle, and the light emission source is turned on only when the at least one particle is being tested during the turn-on time; wherein when the first detection result indicates that a first particle of the at least one particle has arrived at the first detection area, the control module outputs the control signal to the light emission source to turn on the light emission source, and when the second detection result indicates that the first particle has arrived at the second detection area, the control module outputs the control signal to the light emission source to turn off the light emission source; wherein the control module further comprises a counter for recording a first particle number when the first particle of the at least one particle has arrived at the first detection area and a second particle number when the first particle of the at least one particle has arrived at the second detection area to determine to turn on or off the light emission source.

These and other objectives of the present invention will no doubt become obvious to those of ordinary skill in the art after reading the following detailed description of the preferred embodiment that is illustrated in the various figures and drawings.

These and other objectives of the present invention will no doubt become obvious to those of ordinary skill in the art after reading the following detailed description of the preferred embodiment that is illustrated in the various figures and drawings.

DETAILED DESCRIPTION

Figure 1A:
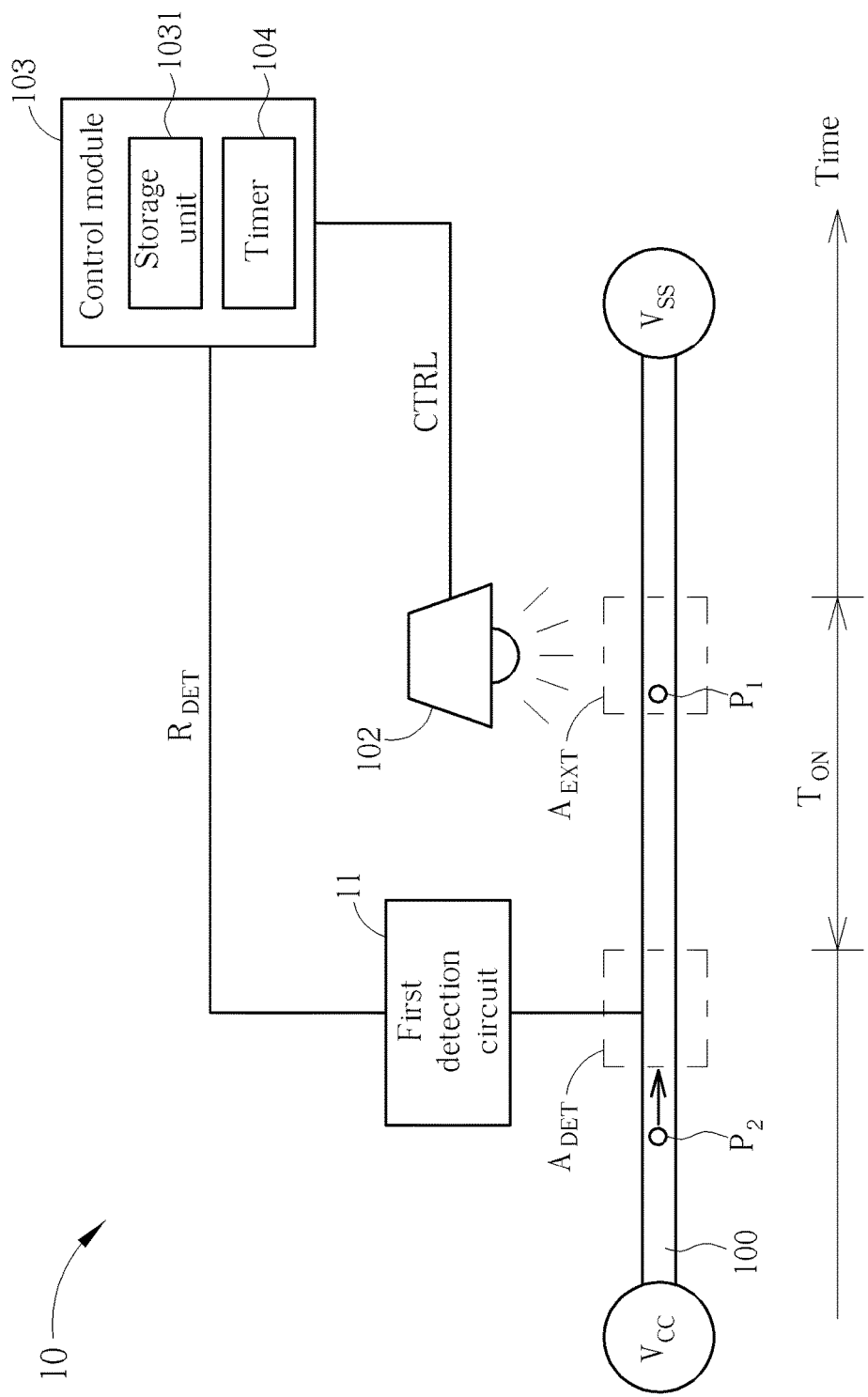
FIG. 1A is a schematic diagram of a biological particle analyzer according to a first embodiment of the present invention.

Please refer to FIG. 1A, which is a schematic diagram of a biological particle analyzer 10 according to a first embodiment of the present invention. The following description takes but not limited to a Flow Cytometer as an example of the biological particle analyzer 10. The biological particle analyzer 10 comprises a microchannel 100, a first detection circuit 11, a light emission source 102 and a control module 103. Two ends of the microchannel 100 are respectively coupled to drive electrodes $V_{CC}$ and $V_{SS}$, the microchannel 100 is used for containing a plurality of particles $P_1$ to flow from an upstream location to a downstream location inside the microchannel 100. The microchannel 100 comprises a first detection area $A_{DET}$ and an excitation area $A_{EXT}$. The first detection circuit 11 is coupled to the first detection area $A_{DET}$ for outputting a first detection result $R_{DET}$ to the control module 103 when at least one particle $P_1$ has arrive at the first detection area $A_{DET}$. The control module 103 is coupled to the first detection circuit 11 and the light emission source 102 for outputting a control signal CTRL to the light emission source 102 according to the first detection result $R_{DET}$, so as to control turning on or off the light emission source 102. The light emission source 102 is coupled to the control module 103 for being turned on according to the control signal CTRL to emit a light to the excitation area $A_{EXT}$ and the particle $P_1$ that has entered the excitation area $A_{EXT}$. The particle $P_1$ is attached to fluorescent chemicals and is excited by the light emission source 102 to emit scatter lights, such that the biological particle analyzer 10 may perform quality and quantity statistical analysis to the particle $P_1$ according to measurement results of the scatter lights attached by fluorescent chemicals.

Specifically, as soon as the first detection result $R_{DET}$ indicates to the control module 103 that the particle $P_1$ has arrived at the first detection area $A_{DET}$, the control module 103 outputs the control signal CTRL to the light emission source 102 to turn on the light emission source 102. The control module 103 performs timing by a built-in timer 104 to calculate a turn-on time $T_{ON}$ of the light emission source 102, to ensure the light emission source 102 is kept turned on during the predetermined turn-on time $T_{ON}$. When the turn-on time $T_{ON}$ has elapsed, the control module 103 turns off the light emission source 102. The turn-on time $T_{ON}$ may be adjusted according to different characteristics of the particle $P_1$, such as volume, electrical charges. As a result, the light emission source 102 is turned on only when the particle $P_1$ is being tested, i.e. turn-on time $T_{ON}$, which saves unnecessary power consumption.

In short, the biological particle analyzer 10 may be notified that the particle $P_1$ is about to pass the excitation area $A_{EXT}$ by the first detection circuit 11 detecting the arrival of the detection area $A_{DET}$, such that the control module 103 turns on the light emission source 102 accordingly. When the turn-on time $T_{ON}$ has elapsed, the control module 103 turns off the light emission source 102. Therefore, the light emission source 102 is turned on only when the particle $P_1$ is being tested, such that the biological particle analyzer 10 may automatically control the turn-on time $T_{ON}$ of the light emission source 102 to achieve smart power savings.

Besides, if the first detection circuit 11 detects another particle $P_2$ has arrived at the detection area $A_{DET}$ during the turn-on time $T_{ON}$ of the light emission source 102, the control module 103 may reset the timer 104 and generate a new turn-on time $T_{ON}$ according to the newly received first detection result $R_{DET}$, such that the light emission source 102 is kept turned on during the new turn-on time $T_{ON}$ to light up the excitation area $A_{EXT}$. As a result, the biological particle analyzer 10 may automatically adjust the turn-on time $T_{ON}$ ON of the light emission source 102 during the test procedure of the particles, which save unnecessary power consumption.

Noticeably, FIG. 1A illustrates one of the embodiments of the present invention, those skilled in the art may make proper modifications and not limited to this embodiment. For example, as well known in the art, the biological particle analyzer 10 works based on Electrokinetics, two ends of the microchannel 100 may be applied drive voltages having opposite polarities according to an electrically charged polarity of the particle $P_1$, a uniform directed electric field may be formed inside the microchannel 100, and the electrically charged particle $P_1$ may be attracted by the electric field to flow inside the microchannel 100, which is called Electrophoresis of an electrically charged particle. If the particle $P_1$ is positive electrically charged, the drive electrode $V_{CC}$ is applied to a positive drive voltage, and the drive electrode $V_{SS}$ is applied to a negative drive voltage. On the contrary, if the particle $P_1$ is negative electrically charged, the drive electrode $V_{CC}$ is applied to a negative drive voltage, and drive electrode $V_{SS}$ is applied to a positive drive voltage. The first detection circuit 11 is preferably a Resistive Pulse Sensor.

Figure 1B:
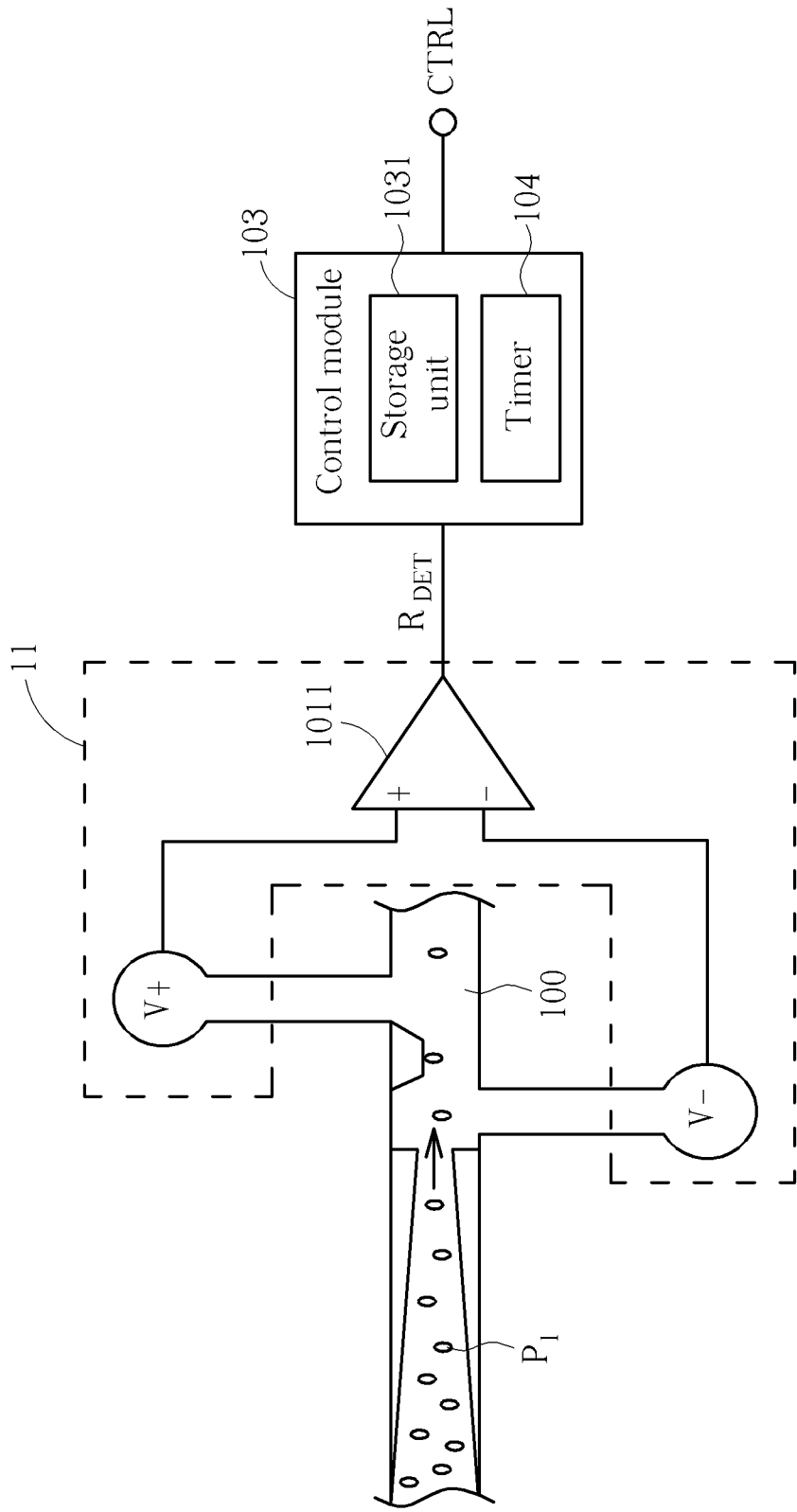
FIG. 1B is a schematic diagram illustrating an operational principle of the first detection circuit shown in FIG. 1A.

Please refer to FIG. 1B, which illustrates an operational principle of the first detection circuit 11. As shown in FIG. 1B, the first detection circuit 11 may be a differential amplifier 1011 including a positive input terminal V+ and a negative input terminal V− coupled to the first detection area $A_{DET}$, and an output terminal for outputting the first detection result $R_{DET}$. A diameter of the microchannel 100 is narrower as the particle $P_1$ flows closer to the first detection area $A_{DET}$, which may align the particles flowing through the microchannel 100 into a serial stream. That is, the first detection area $A_{DET}$ may be passed by the sole single particle $P_1$. Before the particle $P_1$ arrives at the first detection area $A_{DET}$, a voltage difference between the positive input terminal V+ and the negative input terminal V− is a constant. When the particle $P_1$ is passing the first detection area $A_{DET}$, the voltage difference between the positive input terminal V+ and the negative input terminal V− is influenced by an electrical charge of the particle $P_1$ to have a voltage variation, and the differential amplifier 1011 may amplify the voltage variation of the voltage difference to generate the first detection result $R_{DET}$, which is an impulse signal, to the control module 103. In other words, when the particle $P_1$ is passing the first detection area $A_{DET}$, a resistance of the first detection area $A_{DET}$ is changed, such that the first detection circuit 11 is capable of detecting the existence of the particle $P_1$ to output the first detection result $R_{DET}$.

Therefore, the first detection circuit 11 may output different impulse signals, i.e. the first detection result to the control module 103 according to different particle characteristics of the particle $P_1$, such as volume, electrical charge quantity and so on. The control module 103 may further comprise a storage unit 1031 for storing the first detection result R and the turn-on time $T_{ON}$ corresponding to different particle characteristics, such that the control module 103 may select the turn-on time $T_{ON}$ of the light emission source 102 accordingly. As a result, the biological particle analyzer 10 may precisely control the turn-on time $T_{ON}$ of the light emission source 102 according to different particle characteristics.

Figure 1C:
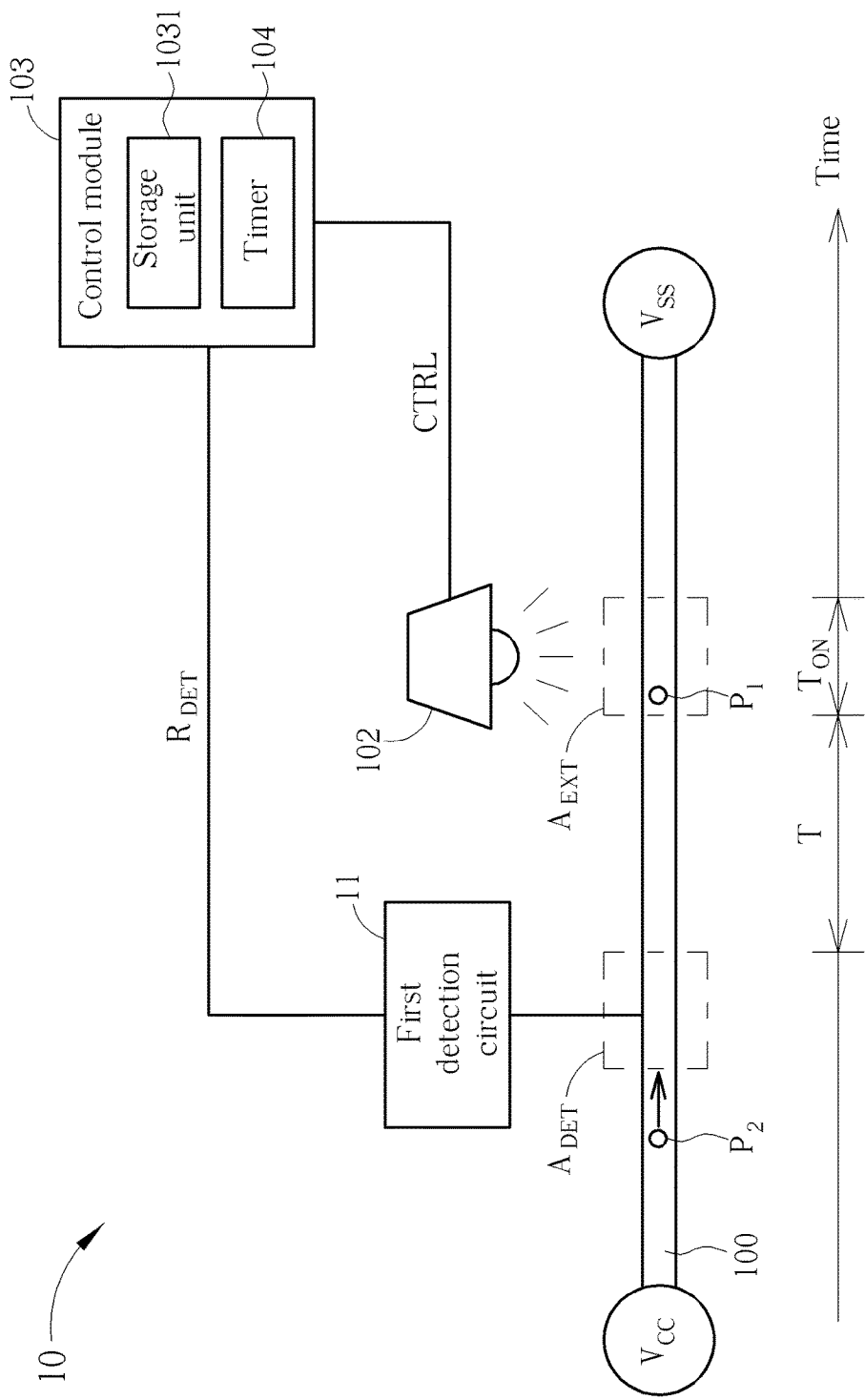
FIG. 1C is a schematic diagram of the biological particle analyzer shown in FIG. 1A according to a second embodiment of the present invention.

The first embodiment describes the light emission source 102 being turned on by the turn-on time $T_{ON}$ as soon as the particle $P_1$ has arrived at the first detection area $A_{DET}$. In the second embodiment of present invention, as shown in FIG. 1C, a difference between the first embodiment and the second embodiment is that there is a delay time T after the particle $P_1$ has arrived at the first detection area $A_{DET}$ and the light emission source 102 is turned on after the delay time T is elapsed. Specifically, the control module 103 may set the delay time T counted by the timer 104, the light emission source 102 is turned on for the predetermined turn-on time $T_{ON}$ when the delay time T elapsed and the particle $P_1$ is going to arrive at the excitation area $A_{EXT}$. The storage unit 1031 may store the delay time T and the turn-on time $T_{ON}$ according to different particle characteristics, and the timer 104 may time the delay time T and the turn-on time $T_{ON}$, which allows the biological particle analyzer 10 to automatically turn on or off the light emission source 102.

Figure 1D:
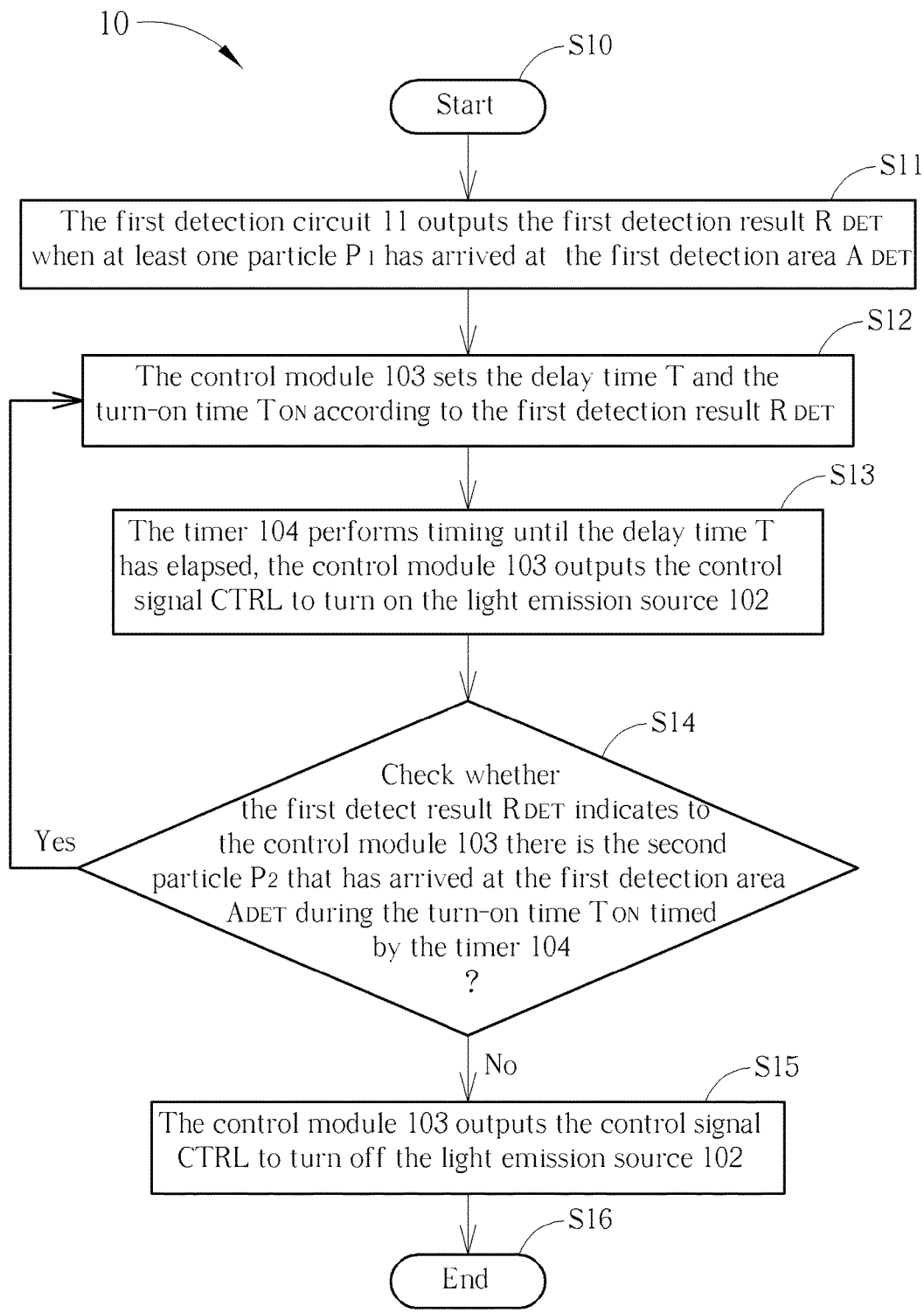
FIG. 1D is a schematic diagram of a biological particle analysis process according to the first and second embodiments of the present invention.

Operations of the biological particle analyzer 10 in the first and second embodiments may be summarized into a biological particle analysis process P10, as shown in FIG. 1D. The biological particle analysis process P10 comprises the following steps: Step S10: Start. Step S11: The first detection circuit 11 outputs the first detection result $R_{DET}$ when at least one particle $P_1$ has arrived at the first detection area $A_{DET}$. Step S12: The control module 103 sets the delay time T and the turn-on time $T_{ON}$ according to the first detection result $R_{DET}$. Step S13: The timer 104 performs timing until the delay time T has elapsed, the control module 103 outputs the control signal CTRL to turn on the light emission source 102. Step S14: Check whether the first detect result $R_{DET}$ indicates to the control module 103 there is the second particle $P_2$ that has arrived at the first detection area $A_{DET}$ during the turn-on time $T_{ON}$ timed by the timer 104. If yes, go to Step S12; if no, go to Step S15. Step S15: The control module 103 outputs the control signal CTRL to turn off the light emission source 102. Step S16: End.

Please note that the steps S10-S15 of the biological particle analysis process P10 are used for the biological particle analyzer 10 shown in FIG. 1C. For the biological particle analyzer 10 shown in FIG. 1A, steps S12 and S13 for setting the delay time T may be omitted, which maybe regarded as the delay time T is zero, i.e. T=0. Details of the biological particle analysis process P10 may be obtained by referring to descriptions of the biological particle analyzer 10, which is omitted herein.

Furthermore, an average velocity of the particle $P_1$ flowing in the microchannel may be calculated to obtain an arrival time of the particle $P_1$ arriving at the excitation area $A_{EXT}$, so as to more precisely determine the turn-on time $T_{ON}$ for turning on the light emission source 102. For example, please refer to FIG. 2A, which is a schematic diagram of a biological particle analyzer 20 according to a third embodiment of the present invention. The biological particle analyzer 20 comprises a microchannel 200, a first detection circuit 21, a second detection circuit 22, a control module 203, a timer 204 and drive electrodes $V_{CC}$ and $V_{SS}$. The first detection circuit 21 is coupled to a the first detection area $A_{DET}$ close to the drive electrode $V_{CC}$ of the microchannel 200, the first detection circuit 21 is used for outputting a the first detection result $R_{DET}$ to the control module 203. The second detection circuit 22 is coupled to a second detection area $A_{DET-2}$ between a downstream location of the first detection area $A_{DET}$ and the excitation area $A_{EXT}$ of the microchannel 20. The second detection circuit 22 is used for outputting a second detection result $R_{DET-2}$ to the control module 203.

Figure 2A:
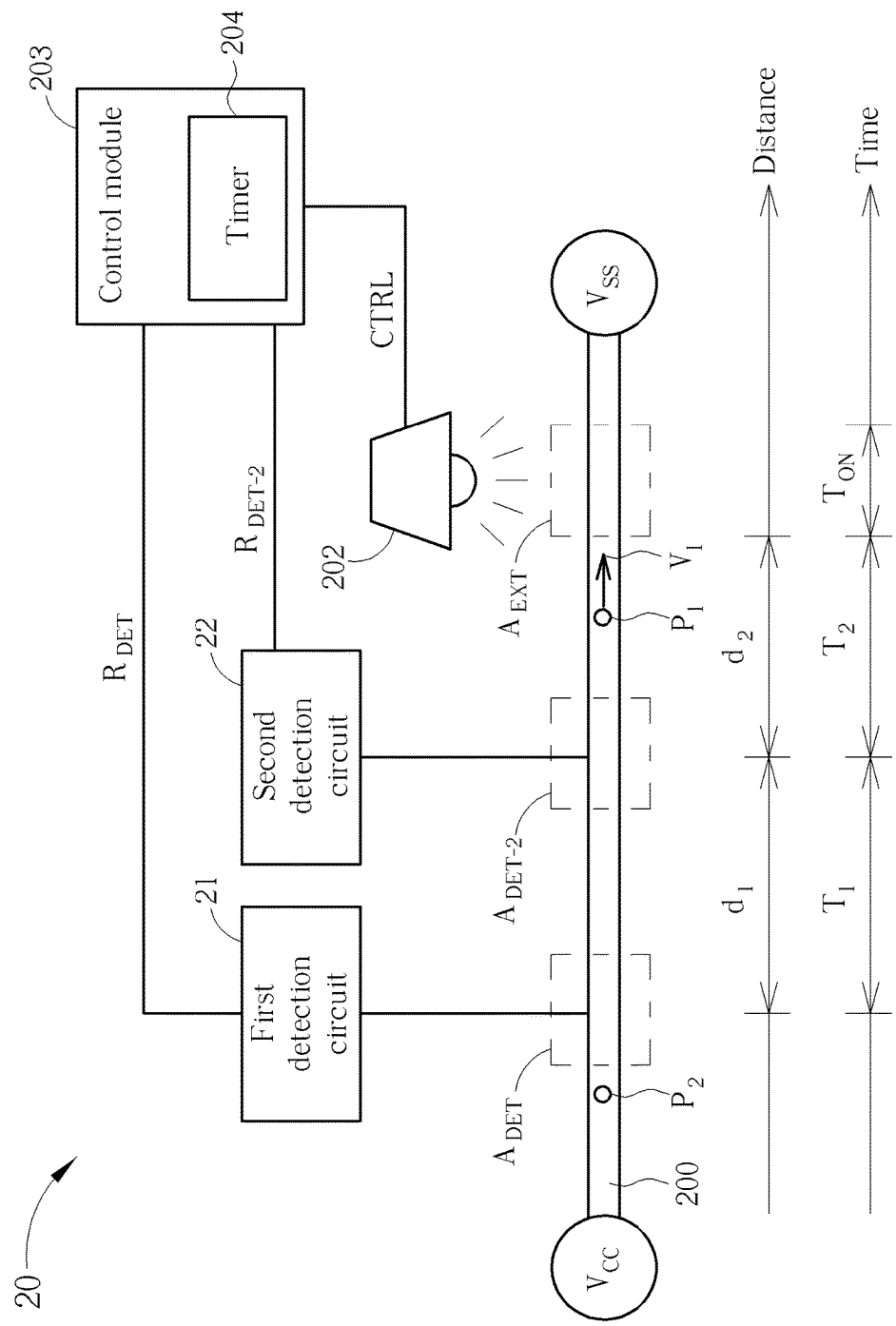
FIG. 2A is a schematic diagram of a biological particle analyzer according to a third embodiment of the present invention.

A shown in FIG. 2A, the second detection area $A_{DET-2}$ is located between the first detection area $A_{DET}$ and the excitation area $A_{EXT}$. There is a distance $d_1$ between the second detection area $A_{DET-2}$ and the first detection area $A_{DET}$ and a distance $d_2$ between the second detection area $A_{DET-2}$ and the excitation area $A_{EXT}$. When the particle $P_1$ sequentially arrives at the first detection area $A_{DET}$ and the second detection area $A_{DET-2}$, the first detection circuit 21 and the second detection circuit 22 respectively outputs the first detection result $R_{DET}$ and the second detection result $R_{DET-2}$ to the control module 203. The control module 203 may calculate an elapsed time $T_1$ of the particle $P_1$ flowing from the first detection area $A_{DET}$ to the second detection area $A_{DET-2}$ according to the first detection result $R_{DET}$ and the second detection result $R_{DET-2}$. The control module 203 may also calculate an average velocity $V_1$ of the particle $P_1$ according to the elapsed time $T_1$ and the distance $d_1$. Specifically, the timer 204 starts timing as soon as the control module 203 receives the first detection result $R_{DET}$, and the timer 204 stops timing when the control module 203 receives the second detection result $R_{DET-2}$, wherein the elapsed time $T_1$ is the time that the particle $P_1$ flowing from the first detection area $A_{DET}$ to the second detection area $A_{DET-2}$. As a result, the control module 203 may calculate the average velocity $V_1$ of the particle $P_1$ according to elapsed time $T_1$ and distance $d_1$, i.e. $V_1=d_1/T_1$. Then, the control module 203 may calculate an arrival time $T_2$ of the particle $P_1$ arriving at the excitation area $A_{EXT}$ according to the average velocity $V_1$ and the distance $d_2$, i.e. $T_2=V_1/d_2$, so that the control module 203 may output the control signal CTRL to turn on the light emission source 202 at the arrival time $T_2$ and keep the light emission source 202 turned on during the turn-on time $T_{ON}$.

Similar to the first embodiment, if the first detection circuit 21 detects another particle $P_2$ has arrived at the detection area before the light emission source 202 is turned off, i.e. during the turn-on time $T_{ON}$, the control module 203 may recalculate the arrival time $T_2$ and extend the turn-on time $T_{ON}$ of the light emission source 202 until the particle $P_2$ has left the excitation area $A_{EXT}$ according to the latest received first detection result $R_{DET}$ and the second detection result $R_{DET-2}$. Noticeably, in practice, the biological particle analyzer 20 may test a plurality of particles at the same time, a designer may adjust the turn-on time $T_{ON}$ to turn on light emission source 202 according to numbers of the plurality of particles. For example, there are at least two cases that may happen when two or more particles $P_1$ and $P_2$ are tested at the same test process.

Case (1): The particle $P_1$ is in the excitation area $A_{EXT}$, which means the light emission source 202 is turned on during the turn-on time $T_{ON}$, and the particle $P_2$ has left the first detection area $A_{DET}$ but has not arrived at the second detection area $A_{DET-2}$. When case (1) happens, although the turn-on time $T_{ON}$ has elapsed, the control module 203 preferably keeps the light emission source 202 turned on until the particle $P_2$ has arrived at the second detection area $A_{DET-2}$. Accordingly the control module 203 may calculate a new arrival time $T_2$ and a new turn-on time $T_{ON}$ to reset the timer 204, and thus the light emission source 202 is kept turned on around $(T_2+T_{ON})$ until the particle $P_2$ is finished testing. If the arrival time $T_2$ of the particle $P_2$ arriving at the excitation area $A_{EXT}$ is too short, e.g. a velocity of the particle $P_2$ is fast, such that the control module 203 may be too late to turn on the light emission source 202, which may cause the light emission source 202 to be turned on and off quickly in a short time, in order to protect the light emission source 202 and related circuits, the control module 203 preferably keeps the light emission source 202 turned on until the particle $P_2$ is finished testing. Therefore, in case (1), a real turn-on time of the light emission source 202 for testing the particles $P_1$ and $P_2$ may be different according to particle characteristics, flowing velocity or locations flowing to the first detection area and the second detection area $A_{DET-2}$.

On the other hand, case (2): The particle $P_1$ remains in the excitation area $A_{EXT}$, which means the light emission source 202 is turned on during the turn-on time $T_{ON}$, and the particle $P_2$ has arrived at the second detection area $A_{DET-2}$, the control module 203 recalculates a new arrival time $T_2$ and a new turn-on time $T_{ON}$. When case (2) happens, the control module 203 may set a new arrival time $T_2$ and a new turn-on time $T_{ON}$ and reset the timer 204 to keep the light emission source 202 turned on around $(T_2+T_{ON})$, until the particle $P_2$ is finished testing. In case (2), the real turn-on times of the light emission source 202 corresponding to the test procedures of the particles $P_1$ and $P_2$ may be different since the particles $P_1$ and $P_2$ may be distinct and have different properties and velocities or locations passing the excitation area $A_{EXT}$.

As a result, the biological particle analyzer 20 may automatically turn on or off the light emission source 102 during the test procedure to save power consumption or prevent fast power switching. Furthermore, besides turning on the light emission source 202 during the turn-on time $T_{ON}$ when the particles $P_1$ and $P_2$ are passing the excitation area $A_{EXT}$, a designer may adjust a time that the light emission source 202 is turned on according to practical test conditions to have a flexible control time for turning on and off the light emission source 202.

Figure 2B:
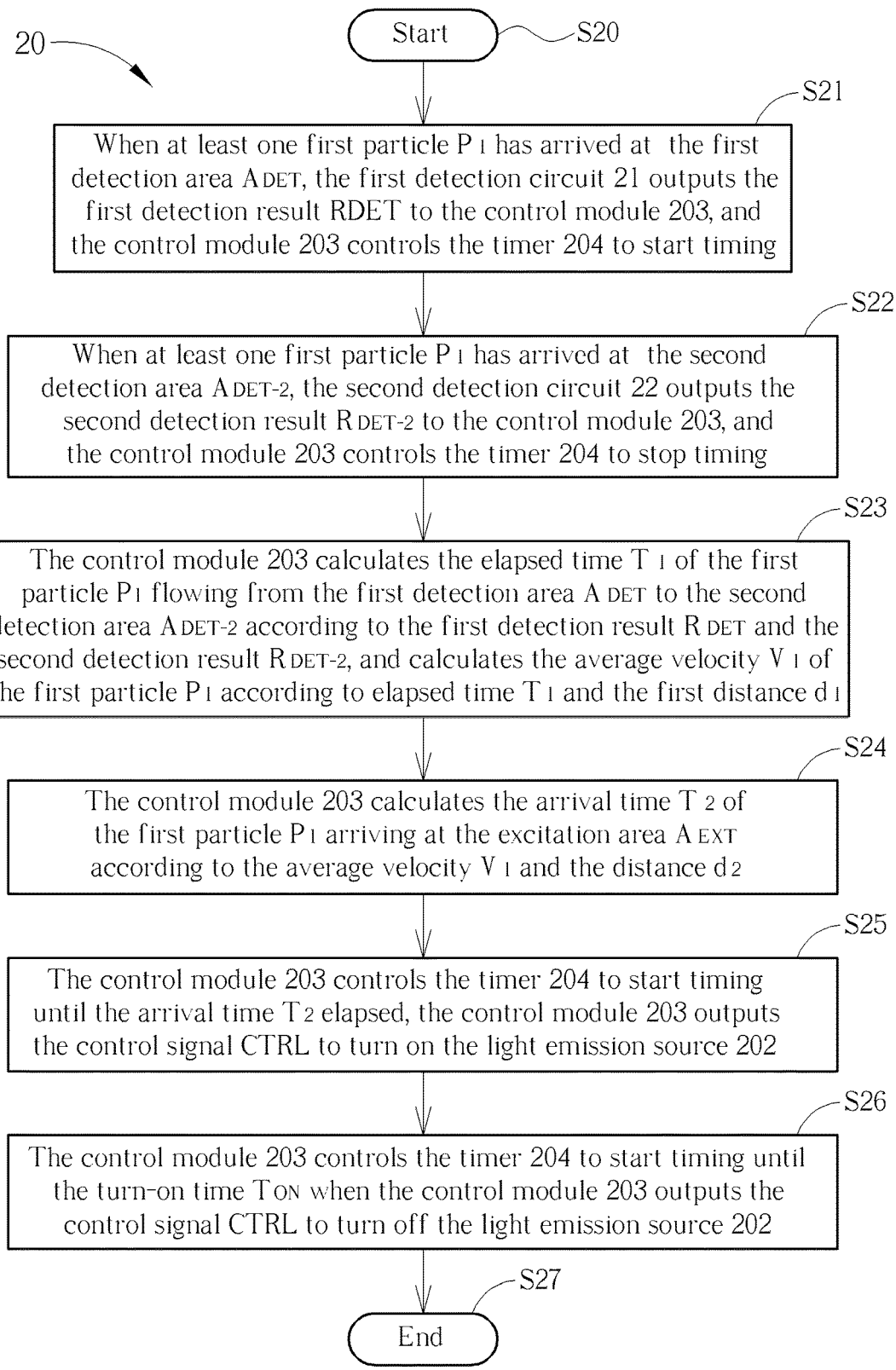
FIG. 2B is a schematic diagram of a biological particle analysis process according to the third embodiment of the present invention.

Operations of the biological particle analyzer 20 in the third embodiment may be summarized into a biological particle analysis process P20, as shown in FIG. 2B. The biological particle analysis process P20 comprises the following steps: Step S20: Start. Step S21: When at least one first particle $P_1$ has arrived at the first detection area $A_{DET}$, the first detection circuit 21 outputs the first detection result $R_{DET}$ to the control module 203, and the control module 203 controls the timer 204 to start timing. Step S22: When a least one first particle $P_1$ has arrived at the second detection area $A_{DET-2}$, the second detection circuit 22 outputs the second detection result $R_{DET-2}$ to the control module 203, and the control module 203 controls the timer 204 to stop timing. Step S23: The control module 203 calculates the elapsed time $T_1$ of the first particle $P_1$ flowing from the first detection area $A_{DET}$ to the second detection area $A_{DET-2}$ according to the first detection result $R_{DET}$ and the second detection result $R_{DET-2}$, and calculates the average velocity $V_1$ of the first particle $P_1$ according to elapsed time $T_1$ and the first distance $d_1$. Step S24: The control module 203 calculates the arrival time $T_2$ of the first particle $P_1$ arriving at the excitation area $A_{EXT}$ according to the average velocity $V_1$ and the distance $d_2$. Step S25: The control module 203 controls the timer 204 to start timing until the arrival time $T_2$ elapsed, the control module 203 outputs the control signal CTRL to turn on the light emission source 202. Step S26: The control module 203 controls the timer 204 to start timing until the turn-on time $T_{ON}$ when the control module 203 outputs the control signal CTRL to turn off the light emission source 202. Step S27: End.

Details of the biological particle analysis process P20 may be obtained by referring to descriptions of the biological particle analyzer 20, which is omitted herein.

Figure 3A:
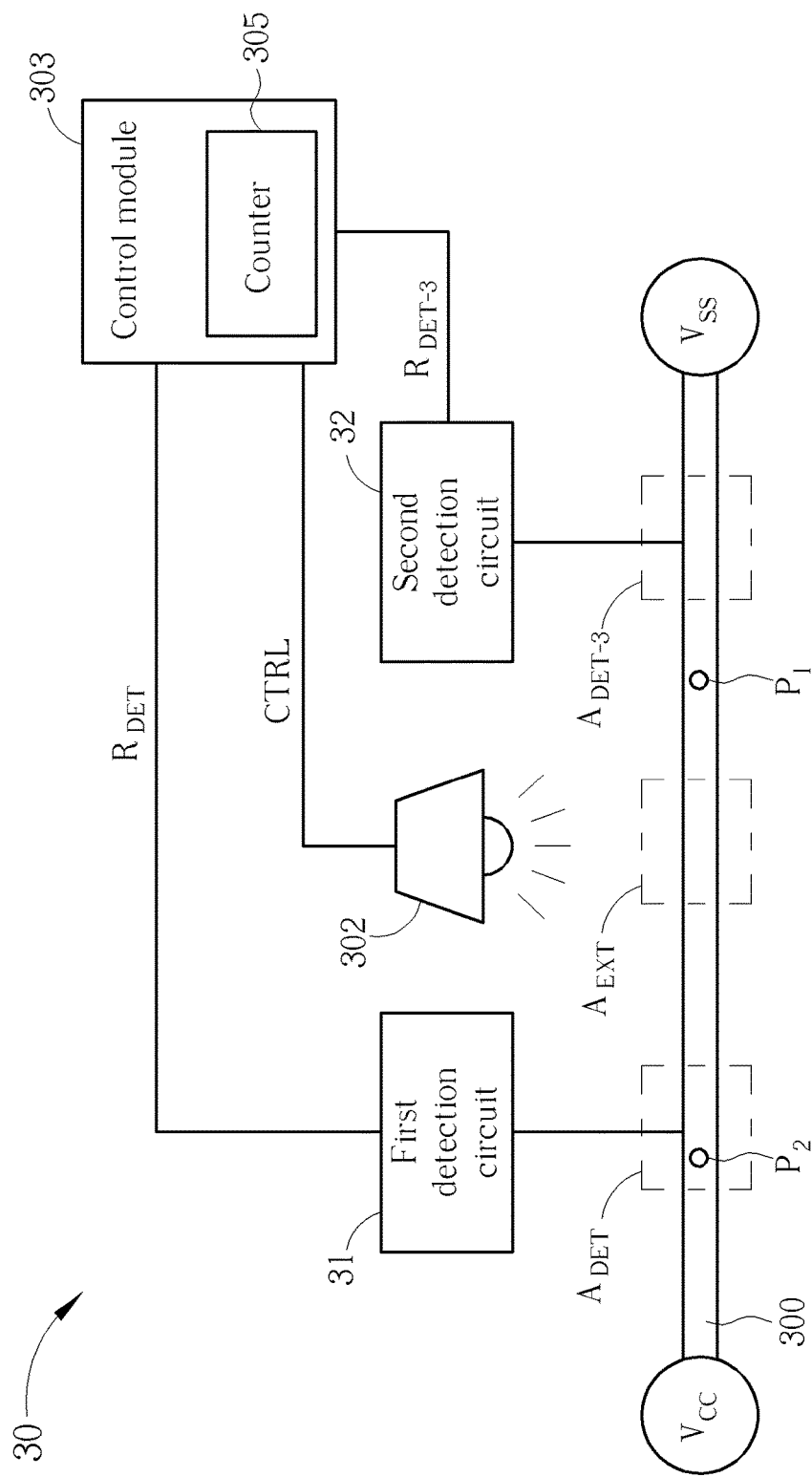
FIG. 3A is a schematic diagram of a biological particle analyzer according to a fourth embodiment of the present invention.

Furthermore, the second detection circuit 22 shown in FIG. 2A may be disposed close to the drive electrode $V_{SS}$ in the microchannel 200 to have another method to determine when to turn on the light emission source 102. Please refer to FIG. 3A, which is a schematic diagram of a biological particle analyzer 30 according to a fourth embodiment of the present invention. As shown in FIG. 3A, a first detection circuit 31 of the biological particle analyzer 30 is coupled to the first detection area $A_{DET}$ close to the drive electrode $V_{CC}$ in the microchannel 300, the first detection circuit 31 is used for outputting the first detection result $R_{DET}$ to control module 303. The second detection circuit 32 is coupled to a detection area $A_{DET-3}$ at a downstream of the excitation area $A_{EXT}$ in the microchannel 300, i.e. the excitation area $A_{EXT}$ is located between the first detection area $A_{DET}$ and the second detection area $A_{DET-3}$.

In such a structure, when the particle $P_1$ has arrived at the first detection area $A_{DET}$, the first detection circuit 31 may output the first detection result $R_{DET}$ to the control module 303. The control module 303 may output the control signal CTRL to the light emission source 302 to turn on the light emission source 302. When the particle $P_1$ has arrived at the second detection area $A_{DET-3}$, the second detection circuit 32 may output the second detection result $R_{DET-3}$ to the control module 303, such that the control module 303 may output the control signal CTRL to the light emission source 302 to turn off the light emission source 302.

Noticeably, the control module 303 may further comprise a counter 305 for respectively counting particle numbers $N_{IN}$ and $N_{OUT}$ when at least one particle has arrived at the first detection area $A_{DET}$ and the second detection area $A_{DET-3}$, so as to determine to turn on or off the light emission source 302. Specifically, when the particle $P_1$ is about to flow in the microchannel 300, the counter 305 defaulted the particle numbers $N_{IN}$ and $N_{OUT}$ to be zero, the detection circuit 301 may detect the particle $P_1$ has arrived at the first detection area $A_{DET}$ and output the first detection result $R_{DET}$ to the control module 303. The control module 303 increases the particle number $N_{IN}$ of the counter 305 by 1, and outputs the control signal CTRL to the light emission source 302 to turn on light emission source 302. When the particle $P_1$ sequentially arrives at the excitation area $A_{EXT}$ and the second detection area $A_{DET-3}$, which means the particle $P_1$ has been fully tested, the second detection circuit 32 may output the second detection result $R_{DET-3}$ to the control module 303, and control module 303 may increase the particle number $N_{OUT}$ of the counter 305 by 1. Therefore, when the particle number $N_{IN}$ is equal to the particle number $N_{OUT}$, i.e. $N_{IN}=N_{OUT}$, the control module 303 may confirm the particle $P_1$ has been fully tested, after which, the control module 303 may output the control signal CTRL to the light emission source 302 to turn off light emission source 302.

For example, when test two or more of the particles $P_1$ and $P_2$, the control module 303 may count the particle number $N_{IN}$ to be 2 to turn on the light emission source 302 according to the first detection result $R_{DET}$ outputted by the first detection circuit 31. Then, the control module 303 counts the particle number $N_{OUT}$ to be 2 according to the second detection result $R_{DET-3}$ outputted by the second detection circuit 32, and outputs the control signal CTRL to the light emission source 302 to turn off the light emission source 302. As a result, the control module 303 may respectively record that the particle numbers $N_{IN}$ and $N_{OUT}$ indicated the particles have arrived at the first detection area $A_{DET}$ and the second detection area $A_{DET-3}$, so as to determine to turn on or off the light emission source 302, which allows the biological particle analyzer 30 to automatically turn on or off the light emission source 302 during the test procedure to reduce power consumption.

Figure 3B:
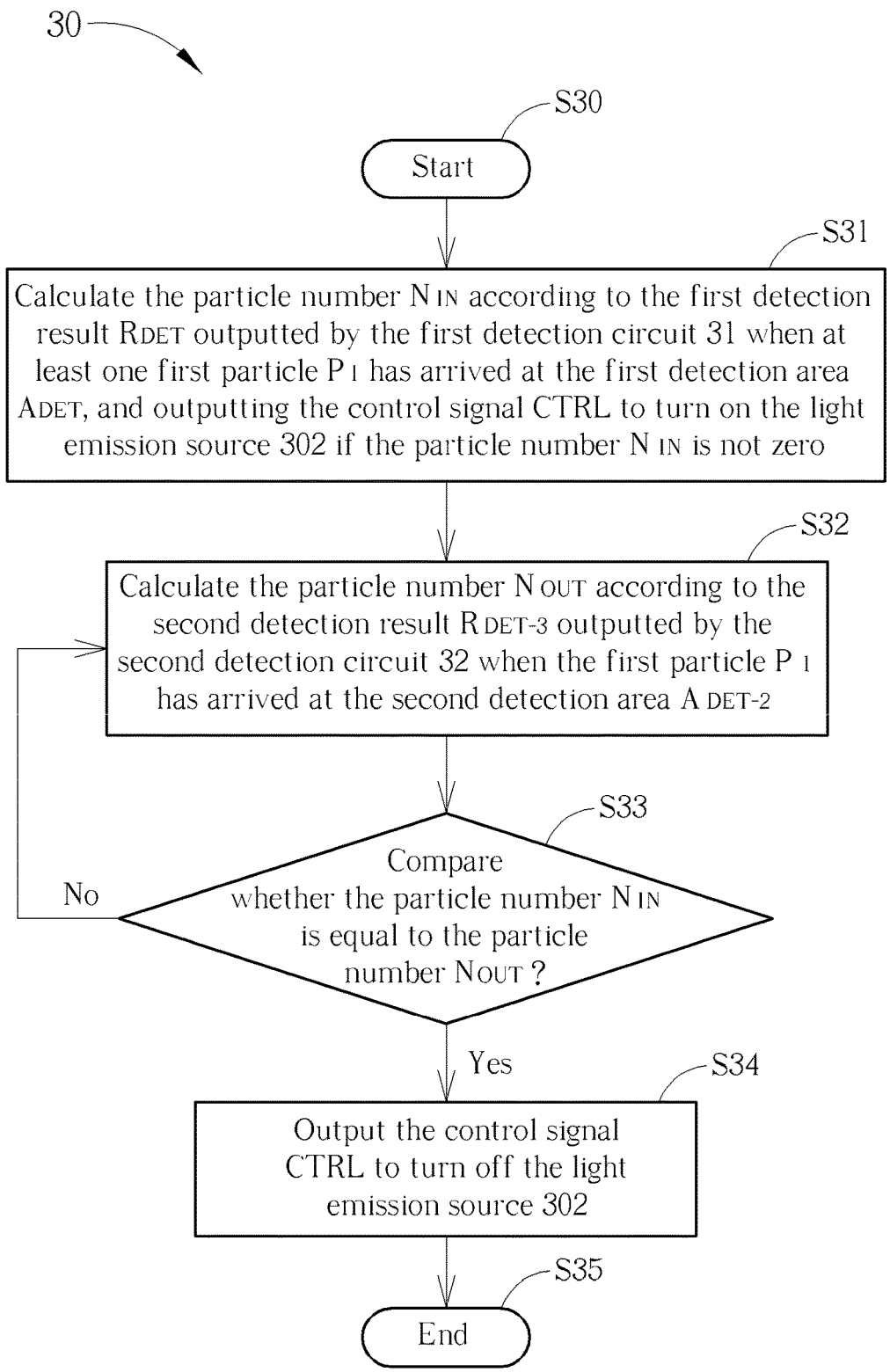
FIG. 3B is a schematic diagram of a biological particle analysis process according to the fourth embodiment of the present invention.

Operations of the biological particle analyzer 30 may be summarized into a biological particle analysis process P30, as shown in FIG. 3B. The biological particle analysis process P30 comprises the following steps: Step S30: Start. Step S31: Calculate the particle number $N_{IN}$ according to the first detection result $R_{DET}$ outputted by the first detection circuit 31 when at least one first particle $P_1$ has arrived at the first detection area $A_{DET}$, and outputting the control signal CTRL to turn on the light emission source 302 if the particle number $N_{IN}$ is not zero. Step S32: Calculate the particle number $N_{OUT}$ according to the second detection result $R_{DET-3}$ outputted by the second detection circuit 32 when the first particle $P_1$ has arrived at the second detection area $A_{DET-2}$. Step S33: Compare whether the particle number $N_{IN}$ is equal to the particle number $N_{OUT}$. If yes, go to Step S34; if no, go to Step S32. Step S34: Output the control signal CTRL to turn off the light emission source 302. Step S35: End.

Details of the biological particle analysis process P30 may be obtained by referring to descriptions of the biological particle analyzer 30, which is omitted herein.

Please note that the timer described in the above mentioned embodiments is built into the control module, which is not limiting, those skilled in the art may realized that the timer may be integrated in other circuits or devices of the biological particle analyzer, as long as the timer may be controlled by the control module to perform counting time and/or clocking.

To sum up, when the traditional biological particle analyzer is operating, the light emission source for emitting a light to the particles consumes most of power of the biological particle analyzer, and the light emission source is often turned on no matter whether a test procedure is being performed, which not only wastes power but also produces a significant amount of heat. The significant amount of heat may reduce battery life, influence usage convenience, deteriorate product reliability and increase production costs. In comparison, the biological particle analyzers 10, 20 and 30 of the present invention may have different detection methods or judgment parameters, such as setting the turn-on time of the light emission source, calculating the average velocity of the particle to evaluate the arrival time of the particle arriving at the light emission source, or calculating the number of the particles to determine to turn on or off the light emission source. Thus, the biological particle analyzers 10, 20 and 30 may automatically turn on or off the light emission source to save unnecessary power consumption, which achieves smart power savings. As a result, the biological particle analyzers 10, 20 and 30 of the present invention may effectively reduce power consumption, extend battery life and increase product reliability, or reduce a volume of a battery, which reduces a size and production cost of the biological particle analyzer and also facilitates a birth of a miniature biological particle analyzer.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of analyzing biological particles for a biological particle analyzer comprising a light emission source and a microchannel for containing a particle flowing inside the microchannel, the microchannel comprising a first detection area at an upstream location, a second detection area located at a downstream location and an excitation area at the downstream location lighted by the light emission source, the method comprising:

by a first detection circuit of the biological particle analyzer, outputting a first detection result when at least one particle has arrived at the first detection area;

by a second detection circuit of the biological particle analyzer, outputting a second detection result to the control module when the particles have arrived at the second detection area; and by a control module of the biological particle analyzer, determining when to turn on or off the light emission source and outputting a control signal to turn on or off the light emission source according to the first detection result;

wherein the control module is configured to calculate a turn-on time according to different particle characteristics and an average velocity of the at least one particle, and the light emission source is turned on only when the at least one particle is being tested during the turn-on time;

wherein when the first detection result indicates that a first particle of the at least one particle has arrived at the first detection area, the control module outputs the control signal to the light emission source to turn on the light emission source, and when the second detection result indicates that the first particle has arrived at the second detection area, the control module outputs the control signal to the light emission source to turn off the light emission source;

wherein the control module further comprises a counter for recording a first particle number when the first particle of the at least one particle has arrived at the first detection area and a second particle number when the first particle of the at least one particle has arrived at the second detection area to determine to turn on or off the light emission source.

2. The method of analyzing biological particles of claim 1, further comprising:

by the control module, setting a turn-on time and performing timing according to the first detection result, such that the light emission source is turned on during the turn-on time; and by the control module, turning off the light emission source when the turn-on time elapsed.

3. The method of analyzing biological particles of claim 2, further comprising:

by the control module, setting a delay time and performing timing according to the first detection result until the delay time has elapsed, and turning on the light emission source during the turn-on time.

4. The method of analyzing biological particles of claim 2, further comprising:

by the control module, generating a new turn-on time according to the first detection result, such that the light emission source keeps turned on to light up the excitation area during the new turn-on time when a first particle has arrived at the first detection area and the light emission source is turned on during the turn-on time, if the first detection result indicates a second particle has arrived at the first detection area.

5. The method of analyzing biological particles of claim 1, wherein the first detection circuit is a Resistive Pulse Sensor.

6. The method of analyzing biological particles of claim 5, wherein two ends of the microchannel are respectively coupled to a first drive electrode and a second drive electrode for driving the particle to flow inside the microchannel.

7. The method of analyzing biological particles of claim 1, wherein the control module further comprises a storage unit for storing the detection result corresponding to different particle characteristics to accordingly set a turn-on time and a turn-off time of the light emission source.

8. The method of analyzing biological particles of claim 1, further comprising:
 calculating an average velocity according to a distance and a time that the particle sequentially arrives at the first detection area and the second detection area;
 calculating an arrival time and setting a turn-on time of the particle according to the average velocity and a distance between the second detection area and the excitation area; and
 outputting the control signal to turn on the light emission source during the turn-on time after the arrival time is elapsed.

9. The method of analyzing biological particles of claim 8, further comprising:
 by the control module, extending the turn-on time of the light emission source until a second particle has arrived at the second detection area to generate the second detection result when a first particle has arrived at the excitation area and the first detection result indicates that the second particle has arrived at the first detection area during the turn-on time; and
 by the control module, setting a new arrival time and a new turn-on time to keep the light emission source turned on during the new arrival time and new turn-on time until the second particle has left the excitation area.

10. The method of analyzing biological particles of claim 8, further comprising:
 by the control module, setting a new arrival time and a new turn-on time to keep the light emission source turned on during the new arrival time and the new turn-on time until the second particle has left the excitation area when a first particle arrived at the excitation area and the second detection result indicates that a second particle arrived at the second detection area during the turn-on time.

11. The method of analyzing biological particles of claim 1, further comprising:
 by the control module, outputting the control signal to turn on the light emission source when the first particle number is not zero.

12. The method of analyzing biological particles of claim 1, further comprising:
 by the control module, comparing the first particle number with the second particle number; and
 by the control module, outputting the control signal to turn off the light emission source if the first particle number is equal to the second particle number.

* * * * *